(12) United States Patent
Jarmusik et al.

(10) Patent No.: US 12,295,932 B2
(45) Date of Patent: May 13, 2025

(54) SUCCINYLCHOLINE CHLORIDE PREFILLED SYRINGE

(71) Applicant: Hikma Pharmaceuticals USA Inc., Berkeley Heights, NJ (US)

(72) Inventors: Keith Jarmusik, Bedford, OH (US); Ragheb M. AbuRmaileh, Bedford, OH (US)

(73) Assignee: Hikma Pharmaceuticals USA Inc., Berkeley Heights, NJ (US)

( * ) Notice: Subject to any disclaimer, the term of this patent is extended or adjusted under 35 U.S.C. 154(b) by 0 days.

(21) Appl. No.: 17/517,808

(22) Filed: Nov. 3, 2021

(65) Prior Publication Data

US 2023/0132721 A1 May 4, 2023

Related U.S. Application Data

(63) Continuation of application No. 17/517,259, filed on Nov. 2, 2021, now abandoned.

(51) Int. Cl.
| | |
|---|---|
| *A61K 31/221* | (2006.01) |
| *A61J 1/20* | (2006.01) |
| *A61K 9/00* | (2006.01) |
| *A61K 31/225* | (2006.01) |
| *A61K 47/02* | (2006.01) |
| *A61M 5/31* | (2006.01) |
| *A61M 5/315* | (2006.01) |
| *A61M 5/50* | (2006.01) |
| *A61M 5/00* | (2006.01) |

(52) U.S. Cl.
CPC ........... *A61K 31/221* (2013.01); *A61J 1/2048* (2015.05); *A61J 1/2096* (2013.01); *A61K 9/0019* (2013.01); *A61K 31/225* (2013.01); *A61K 47/02* (2013.01); *A61M 5/3129* (2013.01); *A61M 5/3134* (2013.01); *A61M 5/31505* (2013.01); *A61M 5/5086* (2013.01); *A61M 5/002* (2013.01)

(58) Field of Classification Search
CPC .. A61K 31/221; A61K 9/0019; A61K 31/225; A61K 47/02; A61J 1/2048; A61J 1/2096; A61M 5/3134; A61M 5/002
See application file for complete search history.

(56) References Cited

U.S. PATENT DOCUMENTS

| | | | |
|---|---|---|---|
| 10,722,453 B1 * | 7/2020 | Soppimath | A61K 31/225 |
| 2012/0123345 A1 * | 5/2012 | Felts | A61M 5/3129 |
| | | | 604/403 |
| 2020/0023117 A1 * | 1/2020 | Maruyama | B65D 81/05 |

FOREIGN PATENT DOCUMENTS

WO    WO-2013170052 A1 * 11/2013 .............. A61J 1/00

OTHER PUBLICATIONS

Larmené-Beld et al., AAPS PharmSciTech (2020) 21:247 (Year: 2020).*
Guidance for Industry, Container Closure Systems for Packaging Human Drugs and Biologics (May 1999), 56 pages.
U.S. Department of Health and Human Services, Guidance for Industry Q3B(R2) Impurities in New Drug Products, Aug. 2006 ICH Revision 3, Aug. 2006, 18 pages.
U.S. Pharmacopoeia, "<1664> Assessment of Drug Product Leachables Associated With Pharmaceutical Packaging/Delivery Systems," retrieved from https://online.uspnf.com/uspnf/document/1_GUID-080B9CD2-A445-44A2-A529-2CC7F86BCC64_3_en-US (official as of Dec. 1, 2020), 12 pages.
Storms, et al., Stability of Succinylcholine Chloride Injection, Intl J. Pharmaceutical Compounding, 7(1):68, Jan./Feb. 2003, 5pgs.
ASHP Injectable Drug Information, Succinylcholine Chloride, p. 1450-51, 2pgs, (2021) ; "Comprehensive Guide to Compatibility and Stability".
BD Medical Pharmaceutical Systems, BD Steriffil Advance™ (2020), 2pgs.
Pramar et al., Chemical stability and adsorption of succinylcholine chloride injections in disposable plastic syringes, Journal of Clinical Pharmacy and Therapeutics (1994), vol. 19, p. 195-198, 4pgs.
West Pharmaceutical Services, WestFluroTec® (2018), 2pgs.
Succinylcholine Chloride Injection Label, Aug. 2021, 16pgs.

* cited by examiner

*Primary Examiner* — Robert S Cabral
(74) *Attorney, Agent, or Firm* — Neal, Gerber & Eisenberg LLP

(57) ABSTRACT

Prefilled syringes containing a succinylcholine chloride composition, where the prefilled syringes comprise a syringe barrel and a syringe tip comprising cyclic olefin monopolymer ("COP") or cyclic olefin copolymer ("COC"). The syringes can also comprise a luer adapter integral with the syringe tip, where the syringe barrel, syringe tip and luer adapter are a single element comprising COP or COC. The succinylcholine chloride compositions include succinylcholine chloride, a tonicity agent and one or more pH adjusters in an aqueous solution having a pH from about 3.0-4.5. The prefilled syringes containing the succinylcholine compositions are storage-stable for extended periods of time at a temperature of 2-8° C., have acceptable physical parameters such as glide force and break force, and make safe and robust connections with needles and needleless luer adapter devices ("NLADs").

32 Claims, 1 Drawing Sheet

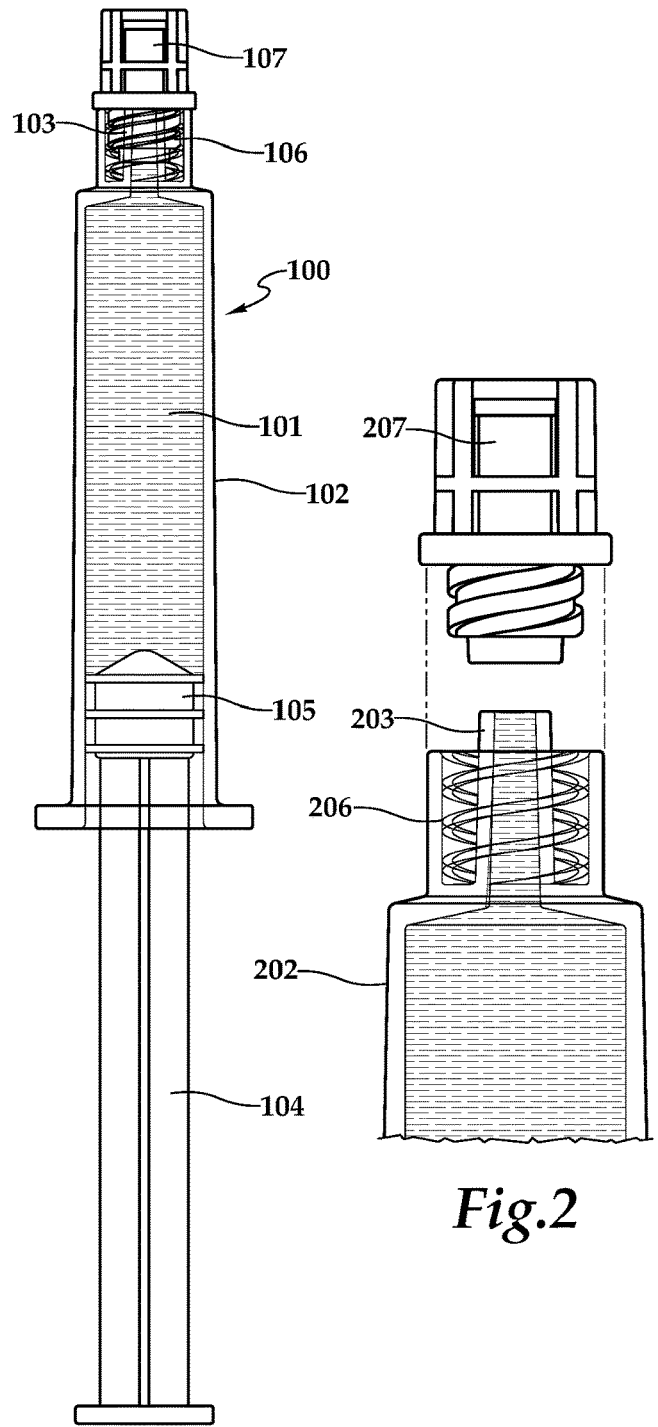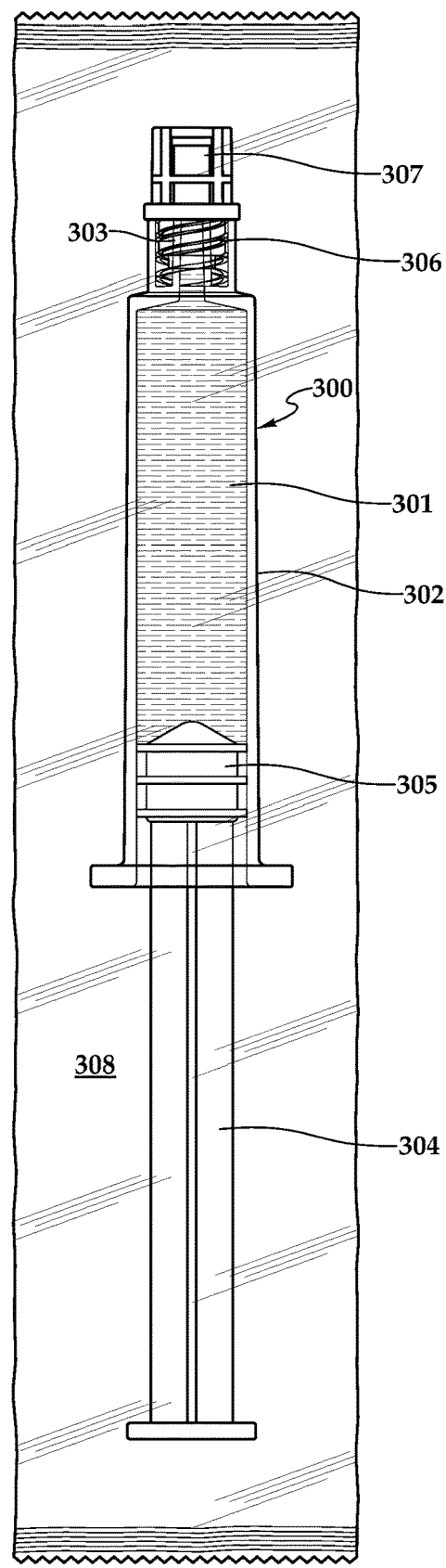
Fig.1
Fig.2
Fig.3

SUCCINYLCHOLINE CHLORIDE PREFILLED SYRINGE

This application is a continuation of U.S. application Ser. No. 17/517,259, which was filed Nov. 2, 2021, the disclosure of which is incorporated by reference in its entirety herein.

The present invention relates to prefilled syringes containing a premixed succinylcholine chloride composition in a syringe comprising a syringe barrel, a syringe tip, a plunger and a plunger stopper, where the barrel and tip comprise a cyclic olefin monopolymer ("COP") or a cyclic olefin copolymer ("COC"). These prefilled syringes are stable upon long-term storage and can be used in emergency situations in conjunction with a needle or a needleless connector for administration to patients in need.

BACKGROUND OF THE INVENTION

Succinylcholine is a depolarizing neuromuscular blocker for use with adults and pediatric patients as an adjunct to general anesthesia, to facilitate tracheal intubation, and to provide skeletal muscle relaxation during surgery or mechanical intubation. It can be used intravenously or intramuscularly.

For years, succinylcholine chloride has been available only in 10 ml glass vials containing 200 mg of succinylcholine chloride. As a result, the hospital pharmacy must use standard disposable syringes to withdraw the desired amount of medication from the vial, remove the needle used for withdrawal, attach a syringe cap, label the syringe with the product details, and then transfer the syringes to the operating room suite, emergency room, or ambulance for use. These steps must be repeated regularly according to hospital policy due to the short in-use stability time after withdrawal of the succinylcholine chloride solution from the vial.

This process has significant drawbacks. Each of the above-noted steps introduces a risk of microbial contamination. Further, the multiple steps involved in this process introduces the potential for significant medication errors, such as improper doses and improper substitution of a different active agent. This puts patients at risk of serious injury, or even death. For example, the label for the succinylcholine chloride vial product, Quelicin®, contains a warning that medication errors with respect to that product may result in paralysis, respiratory arrest, and death.

Further, while the succinylcholine chloride solution in the glass vial is stable for long-term storage when stored at temperatures from 2-8° C., once the vial has been opened and the syringes filled with the succinylcholine chloride solution, the filled syringes have a limited in-use stability time, based on hospital policy.

In an attempt to address these issues, compounding companies, such as 503B outsourcing companies, have manufactured prefilled syringes containing a succinylcholine chloride composition, including syringes containing 5 ml of a succinylcholine chloride composition, where the succinylcholine chloride is present at a concentration of 20 mg/ml. These prefilled syringes are made using the vial product as the starting material. The syringes used for these products are typically plastic syringes comprising polyethylene or polypropylene for the syringe barrel and tip, and have a rubber plunger stopper. These prefilled syringes, however, have a limited shelf-life due to stability issues. Typically, the prefilled syringes must be used within at most 90 days of manufacture. Further, the FDA has warned that the syringes themselves may cause the drug product in the syringe to lose potency over time.

U.S. Pat. No. 10,722,453 ("the '453 patent") discloses a kit comprising a prefilled glass syringe containing a succinylcholine composition. The FDA has indicated that prefilled glass syringes can become clogged and malfunction during the process of connecting them to needleless IV access systems, and as a result has advised that the use of needleless prefilled glass syringes should be avoided in emergency situations if possible. (See https://www.fda.gov/Drugs/DrugSafety/ucm254215.htm.) Moreover, because of recent adverse glass syringe connection events, the FDA has recognized that demonstrating conformity to the ISO 11040-4 standard alone does not ensure that glass syringes can be properly connected to connecting devices. Therefore, sponsors who seek to rely on conformity to ISO 11040-4 in regulatory submissions involving glass syringes must submit information from supplemental tests to show that such syringes can be safely connected.

The '453 patent seeks to address these issues with glass syringes by disclosing the use of a glass syringe having a syringe tip with a larger internal channel than conventional glass syringe tips. It discloses that the use of plastic syringes, such as those made of polypropylene or polyethylene, may cause degradation of the drug product due to leaching of materials from the plastic during storage, particularly where, as is the case with succinylcholine chloride compositions, the pH of the composition is in the acidic range. Although the '453 patent claims to provide a stable and safe kit comprising a prefilled glass syringe containing succinylcholine composition, presently there is no such drug product approved by the FDA. Further, any sponsor desirous of using such a kit will still need to conduct supplemental testing to obtain FDA approval, as discussed above. Moreover, in March 2013, the FDA issued a letter stating that glass syringes having a syringe tip with a larger internal channel than conventional glass syringes can achieve acceptable connections with only certain needles and needleless luer access devices ("NLADs"), but that the potential for malfunction, breaking or clogging can still occur when these glass syringes are used with other needles or NLADs. (See https://www.fda.gov/drug-safety-and-availability/letter-stakeholders-update-certain-needleless-prefilled-glass-syringes.) Thus, even where these glass syringes having a syringe tip with a larger internal channel than conventional glass syringe tips are used, there are still significant safety issues present.

SUMMARY OF THE INVENTION

To address these issues, the inventors have discovered that a prefilled syringe containing a premixed succinylcholine chloride composition where the syringe barrel and syringe tip comprise a cyclic olefin monopolymer ("COP") or a cyclic olefin copolymer ("COC") has long-term stability and is safe for use, including with needles and needleless connectors, such as NLADs. Use of the prefilled syringe of the invention avoids the issues discussed above involving glass syringes, as well as breakage issues inherent in their use.

BRIEF DESCRIPTION OF THE DRAWINGS

FIG. 1 shows a prefilled syringe for use in the present invention.

FIG. 2 shows an expanded view of the distal end of a prefilled syringe for use in the present invention.

FIG. 3 shows a prefilled syringe for use in the present invention enclosed within a flexible plastic overwrap.

DETAILED DESCRIPTION

The prefilled syringe of the present invention contains a premixed succinylcholine chloride composition. Here, "premixed" means that the succinylcholine chloride composition is prepared using bulk succinylcholine chloride, as opposed to being prepared from a sterile solution containing a succinylcholine chloride composition, such as those made by 503B compounding companies. The premixed succinylcholine chloride composition comprises succinylcholine chloride, a tonicity agent, one or more pH adjusting agents, and water for injection. The composition may also include one or more preservatives, such as methylparaben, propylparaben, or a combination thereof. In one embodiment, however, the succinylcholine chloride composition is free of preservatives.

The succinylcholine chloride is present in the prefilled syringe at a concentration from about 10 mg/ml to about 30 mg/ml, or from about 15 mg/ml to about 20 mg/ml. In one embodiment, it is present at a concentration of about 20 mg/ml.

The tonicity agent may be selected from the group consisting of dextrose, mannitol, potassium chloride, and sodium chloride. In some embodiments, the tonicity agent is present in an amount sufficient to make the composition isotonic. In some embodiments, the tonicity agent is present in the composition in an amount sufficient to provide an initial osmolality of from about 280 mOsm/kg to about 340 mOsm/kg. Use of the term "initial" with respect to a given parameter such as osomolality, pH, succinylcholine chloride content, or impurities refers to that parameter at the time the succinylcholine chloride composition is filled into the syringe. In another embodiment, the succinylcholine chloride composition in the prefilled syringe has an osmolality of from about 280 mOsm/kg to about 340 mOsm/kg upon storage for up to fifteen months, or up to eighteen months, at 2-8° C. In a further embodiment, the tonicity agent is sodium chloride, and is present in an initial amount of from about 4 mg/ml to about 7 mg/ml. In another embodiment, the sodium chloride is present in an initial amount from about 4 mg/ml to about 5 mg/ml. In yet another embodiment, the sodium chloride is present in an initial amount of about 4.5 mg/ml.

The pH adjusting agent is selected from the group consisting of acidifying agents, alkalizing agents, and buffering agents, or combinations thereof. In some embodiments, the pH adjusting agent is selected from the group consisting of one or more of citric acid, acetic acid, hydrochloric acid, sodium hydroxide, sodium citrate, potassium hydroxide, and potassium citrate. In one embodiment, the pH adjusting agent is hydrochloric acid, sodium hydroxide, or a combination thereof. In some embodiments, the pH adjusting agent is present in an amount sufficient to provide an initial pH of about 3 to about 4.5. In another embodiment, the pH adjusting agent is present in an amount sufficient to provide an initial pH of about 3.3 to about 3.8. In a further embodiment, the pH of the succinylcholine chloride composition in the prefilled syringe is from about 3 to about 4.5, or from about 3.3 to about 3.8, upon storage for up to fifteen months, or up to eighteen months, at 2-8° C.

The premixed succinylcholine chloride composition may also contain additional excipients, such as non-aqueous solvents or excipients including cyclodextrins, such as β-cyclodextrins, propylene glycol, polyethylene glycols ("PEGs") of varying molecular weight, and glycerin. These additional excipients can be present in the composition in amounts up to 80%. Specifically, glycerin can be present in amounts of from about 1.6-70%, by weight of the composition PEG 300 can be present in amounts from about 50-65% by weight, PEG 400 can be present in amounts of from about 11.2-67% by weight, and propylene glycol can be present in amounts from 0.0025-80% by weight.

Referring to FIG. 1, the premixed succinylcholine chloride composition 101 is contained in a syringe 100 comprising a syringe barrel 102, syringe tip 103, plunger rod 104, and plunger rod stopper 105. The syringe barrel 102 and syringe tip 103 comprise COP or COC, and are preferably a single element. The plunger rod 104 is comprised of a plastic, and in one embodiment comprises polypropylene. In one embodiment, the plunger rod stopper 105 comprises bromobutyl rubber, chlorobutyl rubber, or an elastomer coated with a film comprising poly(ethylene tetrafluoroethylene) ("ETFE"). In another embodiment, the syringe has a luer adapter 106 integral with the syringe tip 103. In a further embodiment, the syringe further comprises a tip cap 107. The tip cap 107 comprises a plastic shell and an elastomer, such as bromobutyl or chlorobutyl rubber, that is fit over the syringe tip 103 by friction or that screws onto the luer adapter 106. In one embodiment, the plastic shell comprises polypropylene. In a further embodiment, the tip cap 107 can comprise an elastomer coated with an ETFE film. Syringes for use in the present invention include Sterifill Advance™ prefillable syringes, available from Becton-Dickinson, and TopPac® prefillable syringes, available from Schott. Tip caps for use in the present invention include those available from Aptar, such as the Aptar 6422GS tip cap, where the elastomer comprises chlorobutyl rubber, as well as those available from Datwyler, such as the Datwyler FM257 tip cap, where the elastomer comprised bromobutyl rubber.

In a further embodiment, and as shown for example in FIG. 2, the syringe barrel 202, syringe tip 203, and luer adapter 206 are a single element comprising COP or COC. For example, the syringe barrel, syringe tip, and luer adapter can be made from a single mold. FIG. 2 also shows a tip cap 207 with threads that can be screwed onto the threads on luer adapter 206.

The premixed succinylcholine chloride compositions in the prefilled syringes of the invention are stable upon long term storage at 2-8° C. In one embodiment, the composition retains at least about 90% of the initial amount of succinylcholine chloride in the composition upon storage for up to fifteen months, or up to eighteen months, at 2-8° C. as determined by High Performance Liquid Chromatograghy ("HPLC"). In another embodiment, the total impurities present are not more than 8%, or not more than 6.5% by weight of the composition, upon storage for up to fifteen months, or up to eighteen months, at 2-8° C. as determined by HPLC. In a further embodiment, the impurities succinic acid and succinylmonocholine chloride are present in an amount not more than 0.2% and 4.0% by weight of the composition, respectively, upon storage for up to fifteen months, or up to eighteen months, at 2-8° C. as determined by HPLC. In yet another embodiment, the impurity choline chloride is present in an amount not more than 2.5% by weight of the composition upon storage for up to fifteen months, or up to eighteen months, at 2-8° C. as determined by Ion Chromatograhpy ("IC").

Additionally, the premixed succinylcholine chloride compositions in the prefilled syringes of the invention are stable when stored at room temperature for up to 14 days after previous long-term storage for up to fifteen months, or up to eighteen months, at 2° to 8° C. In one embodiment, the composition retains at least about 90% of the initial amount of succinylcholine chloride in the composition upon storage for at room temperature for up to 14 days as determined by HPLC. In another embodiment, the total impurities present are not more than 8%, or not more than 6.5% by weight of the composition, upon storage at room temperature for up to 14 days as determined by HPLC. In a further embodiment, the impurities succinic acid and succinylmonocholine chloride are present in an amount not more than 0.2% and 4.0% by weight of the composition, respectively, upon storage at room temperature for up to 14 days as determined by HPLC. In yet another embodiment, the impurity choline chloride is present in an amount not more than 2.5% by weight of the composition, upon storage at room temperature for up to 14 days as determined by IC.

A concern with the use of plastic for prefilled syringes designed to be storage-stable for an extended period of time is that chemicals in the plastic will over time leach into the composition contained in the syringe. For example, the '453 patent discloses that prefilled glass syringes are especially advantageous in avoiding leachables with drug compositions like succinylcholine chloride compositions, particularly where the pH of the drug composition is less than 5.0. (See '453 patent at col. 7, lines 28-35.) However, the prefilled syringes of the present invention containing a premixed succinylcholine chloride composition exhibit only minimal formation of leachables upon extended storage for a period of up to fifteen months, or up to eighteen months, at a temperature of 2° C. to 8° C. Any such leachables are present in a level below the Permitted Daily Exposure (PDE) with a high Margin of Safety (MOS). As a result, no specifications for leachables are warranted or necessary with respect to the prefilled syringes of the present invention containing a premixed succinylcholine chloride composition.

The prefilled syringes of the invention also exhibit superior physical attributes. In one embodiment, upon storage for up to fifteen months, or up to eighteen months, at a temperature of 2° C. to 8° C., the prefilled syringes have a break force of less than 20 N, or less than 11 N, and a glide force of less than 7 N, or less than 3 N, when measured according to ISO 11040-6 and ISO 11040-8. Further, and unlike many glass syringes having non-integral luer adapter, the prefilled syringes of the present invention exhibit a safe and robust connection with NLADs. For example, upon storage for up to fifteen months, or up to eighteen months, at a temperature of 2° C. to 8° C., the prefilled syringes of the present invention having a luer adapter integral with the syringe tip show no evidence of product leakage, air leakage, damage to the syringe, or damages to the NLAD connector when tested according to ISO 80369-7, *Small-bore connectors for liquids and gases in healthcare applications—Part 7: Connectors for intravascular or hypodermic applications.*

The prefilled syringes containing the succinylcholine chloride composition can be provided as a kit, where it is packaged in a clear, flexible plastic overwrap, as shown in FIG. 3. FIG. 3 shows a syringe 300 containing a succinylcholine chloride composition 301, the syringe comprising syringe barrel 302, syringe tip 303, plunger rod 304, plunger rod stopper 305, luer adapter 306, and tip cap 307, packaged in a clear flexible overwrap 308. In one embodiment, the overwrap 308 comprises a polyester film, such as that available form Amcor under the tradename Amcor RBA-008. The overwrap protects the prefilled syringes from physical damage resulting from shipping and handling, and also provides evidence of potential product tampering, for example, if the overwrap is open or has a slit or tear in it.

Procedures for filling the succinylcholine chloride composition into a syringe, and their subsequent processing, such as aseptic filling conditions, are known in the art. In one embodiment, the succinylcholine chloride composition is sterile filtered, and then aseptically filled into the syringes.

The succinylcholine chloride compositions in the prefilled syringes of the invention can be used for both intravenous and intramuscular injections in a bolus dose without dilution. In situations where continuous intravenous infusion is desired, the succinylcholine composition in the prefilled syringe may be diluted to a concentration of from about 1 mg/ml to about 2 mg/ml in a solution such as 5% Dextrose Injection, USP or 0.9% Sodium Chloride Injection, USP. This diluted solution is stable for up to 24 hours when stored at 2-8° C.

The present invention is further described in the following examples. The examples should not, however, be viewed as limiting the scope of the invention.

Example 1

A premixed succinylcholine chloride composition was prepared in bulk and filled into 5 ml BD Sterifill Advance™ prefillable syringes, with the syringe barrel, syringe tip, and luer adapter being a single element comprising COP, a plunger rod comprising polypropylene, and a plunger rod stopper comprising bromobutyl rubber. The syringe tip was covered by an Aptar 6422GS tip cap, where the elastomer is chlorobutyl rubber. After the premixed succinylcholine composition was prepared, it was sterile filtered through two 0.22 μm PVDF membrane capsule filters. The composition was then aseptically filled into the prefillable syringes. The premixed succinylcholine chloride composition is set forth in Table 1 below.

TABLE 1

| Ingredient | Function | Amount |
|---|---|---|
| Succinylcholine chloride USP | active ingredient | 20 mg/ml |
| Sodium chloride USP | tonicity agent | 4.5 mg/ml |
| Hydrochloric acid | pH adjuster | q.s. to a pH of 3.0-4.5 |
| Sodium hydroxide | pH adjuster | q.s. to a pH of 3.0-4.5 |
| Water for Injection | diluent | q.s. to 5 ml |

Example 2

Prefilled syringes prepared according to the method of Example 1 were stability tested over a six-month period at 25° C. and 60% relative humidity. The premixed succinylcholine chloride compositions in the syringes were then tested for succinylcholine chloride content and for chemical impurities using HPLC and/or IC. The compositions were also tested for sterility using USP <71> and for bacterial endotoxins using USP <85>. The prefilled syringes containing the premixed succinylcholine chloride compositions were also subjected to physical testing, such as break force and glide force, all of which were performed according to ISO 11040-6 and ISO 11040-8. The results are set forth in Table 2 below.

TABLE 2

| Accelerated Stability (25° C.+/−2° C.) for Succinylcholine Chloride Injection, USP | | | | | |
|---|---|---|---|---|---|
| Test | Initial | 1 M Horizontal | 1 M Upright | 2 M Horizontal | 2 M Upright |
| Succinylcholine Chloride | 99.0% | 95.7% | 96.3% | 92.3% | 92.9% |
| Choline Chloride | 0.06% | 1.67% | 1.67% | 2.70% | 2.72% |
| Succinic Acid | Not detected (ND) | 0.12% | 0.12% | 0.24% | 0.24% |
| Succinylmonocholine | 0.14% | 2.75% | 2.76% | 3.97% | 4.00% |
| Total Degradants | 0.2% | 4.5% | 4.6% | 7.0% | 7.0% |
| pH | 3.8 | 3.3 | 3.3 | 3.3 | 3.2 |
| Break Force | 4N | 5N | 5N | 5N | 6N |
| Mean Glide Force | 2N | 2N | 2N | 2N | 2N |
| Bacterial Endotoxin | <6.0 EU/mL | Not tested (NT) | NT | NT | NT |
| Sterility | Sterile | NT | NT | NT | NT |
| Test | Initial | 3 M Horizontal | 3 M Upright | 6 M Horizontal | 6 M Upright |
| Succinylcholine Chloride | 99.0% | 89.6% | 89.3% | 83.2% | 83.9% |
| Choline Chloride | 0.06% | 3.88% | 3.92% | 6.96% | 6.79% |
| Succinic Acid | ND | 0.60% | 0.60% | 1.41% | 1.42% |
| Succinylmonocholine | 0.14% | 6.1% | 6.1% | 8.97% | 9.01% |
| Total Degradants | 0.2% | 10.8% | 10.8% | 17.2% | 17.4% |
| pH | 3.8 | 3.1 | 3.1 | 3.1 | 3.1 |
| Break Force | 4N | 5N | 5N | 6N | 5N |
| Mean Glide Force | 2N | 2N | 2N | 2N | 2N |
| Bacterial Endotoxin | <6.0 EU/mL | <6.0 EU/mL | <6.0 EU/mL | <27.0 EU/mL | <27.0 EU/mL |
| Sterility | Sterile | Sterile | Sterile | Sterile | Sterile |

Example 3

Prefilled syringes prepared according to the method of Example 1 were stability tested over a fifteen-month period at a temperature of 2° C. to 8° C. The premixed succinylcholine chloride compositions in the syringes were then tested for succinylcholine chloride content and chemical impurities using HPLC and/or IC. The compositions were also tested for sterility using USP <71> and for bacterial endotoxins using USP <85>. The prefilled syringes containing the premixed succinylcholine chloride compositions were also subjected to physical testing, such as break force and glide force, both of which were performed according to ISO 11040-6 and ISO 11040-8). The prefilled syringes were also tested for positive pressure liquid leakage, stress-cracking, sub-atmospheric air leakage, resistance to axial load, resistance to unscrewing, and resistance to overriding as set forth in ISO 80369-7, *Small-bore connectors for liquids and gases in healthcare applications—Part 7: Connectors for intravascular or hypodermic applications*. The results are set forth in Table 3 below.

TABLE 3

| Long Term Stability (2-8° C.) for Succinylcholine Chloride Injection, USP | | | | | | |
|---|---|---|---|---|---|---|
| Test | Initial | 3 M Horizontal | 3 M Upright | 6 M Horizontal | 6 M Upright | 9 M Horizontal |
| Succinylcholine Chloride | 99.0% | 99.1% | 99.1% | 98.1% | 98.2% | 94.9% |
| Choline Chloride | 0.06% | 0.42% | 0.41% | 0.61% | 0.57% | 1.00% |
| Succinic Acid | ND | <0.05% | <0.05% | <0.05% | <0.05% | 0.08% |
| Succinylmonocholine | 0.14% | 0.95% | 1.11% | 1.35% | 1.31% | 2.09% |
| Total Degradants | 0.2% | 1.4% | 1.5% | 2.0% | 1.9% | 3.4% |
| pH | 3.8 | 3.5 | 3.5 | 3.5 | 3.5 | 3.4 |
| Break Force | 4N | 5N | 4N | 4N | 4N | 5N |
| Mean Glide Force | 2N | 2N | 2N | 2N | 2N | 2N |
| Bacterial Endotoxin | <6.0 EU/mL | NT | NT | NT | NT | NT |
| Sterility | Sterile | NT | NT | NT | NT | NT |
| Test | Initial | 9 M Upright | 12 M Horizontal | 12 M Upright | 15 M Horizontal | 15 M Upright |
| Succinylcholine Chloride | 99.0% | 95.1% | 94.5% | 95.5% | 95.0% | 94.4% |
| Choline Chloride | 0.06% | 0.98% | 1.46% | 1.43% | 1.76% | 1.71% |
| Succinic Acid | ND | 0.08% | 0.12% | 0.11% | 0.14% | 0.14% |
| Succinylmonocholine | 0.14% | 2.07% | 2.95% | 2.90% | 3.32% | 3.30% |
| Total Degradants | 0.2% | 3.3% | 4.6% | 4.5% | 5.3% | 5.2% |
| pH | 3.8 | 3.4 | 3.3 | 3.3 | 3.3 | 3.3 |
| Break Force | 4N | 6N | 5N | 5N | 6N | 5N |
| Mean Glide Force | 2N | 2N | 2N | 2N | 2N | 2N |
| Bacterial Endotoxin | <6.0 EU/mL | NT | <27.0 EU/mL | <27.0 EU/mL | <27.0 EU/mL | <27.0 EU/mL |
| Sterility | Sterile | NT | Sterile | Sterile | Sterile | Sterile |

These results indicate that the succinylcholine compositions in the prefilled syringe are chemically stable after storage for a fifteen-month period at a temperature of 2 to 8° C. Further, the glide force and break force were also acceptable. While not shown in the table, the prefilled syringes showed no evidence of product leakage, air leakage, damage to the syringe, or damages to the NLAD connector after storage for a fifteen-month period at a temperature of 2° C. to 8° C. when tested according to ISO 80369-7, *Small-bore connectors for liquids and gases in healthcare applications—Part 7: Connectors for intravascular or hypodermic applications.*

These results also indicate that the succinylcholine chloride composition in the prefilled syringe would be chemically stable for an eighteen-month period at a temperature of 2 to 8° C., and that the syringes would also have acceptable glide force, break force, and connectivity parameters upon storage at these same conditions.

Example 4

The premixed succinylcholine chloride composition of Example 1 was prepared and sterile filtered through two 0.22 μm PVDF membrane capsule filters. The composition was then aseptically filled into 5 ml Schott TopPac® prefillable syringes, with the syringe barrel, syringe tip, and luer adapter being a single element comprising COC, a plunger rod comprising polypropylene, and a plunger rod stopper comprising bromobutyl rubber. The syringe tip was covered by a Datwyler FM257 tip cap, where the elastomer is bromobutyl rubber. The prefilled syringes were then stability tested for three months at 25° C. and 60% RH, or for six months at 2° C. to 8° C. The premixed succinylcholine chloride compositions in the syringes were then tested for succinylcholine chloride content chemical and impurities using HPLC and/or IC. The prefilled syringes containing the premixed succinylcholine chloride compositions were also subjected to physical testing, such as break force and glide force, tip cap burst resistance, both of which were performed according to ISO 11040-6 and ISO 11040-8. The results are set forth in Table 4.

mean break force, were also acceptable. These results indicate that the prefilled syringes of Example 4 would be stable and the physical parameters would be acceptable when stored at 2° C. to 8° C. for fifteen months, or 18 months.

Example 5

Prefilled syringes prepared according to the method of Example 1 were stored upright for stability testing over a period of twelve months at a temperature of 2° C. to 8° C. They were then stored at room temperature for fourteen days. The premixed succinylcholine chloride compositions in the syringes were tested after both twelve months of storage at 2° C. to 8° C. and fourteen days of storage at room temperature for succinylcholine chloride content and chemical impurities using HPLC and/or IC. The results are set forth in Table 5 below, with the baseline results being those after storage for twelve months at a temperature of 2° C. to 8° C.

TABLE 5

14-Day Room Temperature Stability Results

| Test | Initial (Baseline) | 14-Day Room Temperature Stability |
|---|---|---|
| pH | 3.3 | 3.3 |
| Succinylcholine Chloride | 94.7% | 92.9% |
| Choline Chloride | 1.44% | 2.13% |
| Succinic Acid | 0.12% | 0.22% |
| Succinylmonocholine Chloride | 2.93% | 3.98% |
| Total Degradants | 4.6% | 6.4% |

The results indicate that the succinylcholine chloride composition in the prefilled syringes were chemically stable for up to 14 days of storage at room temperature preceded by twelve months of storage at 2° C. to 8° C. They also indicate that the succinylcholine chloride composition in the prefilled syringes would be chemically stable for up to 14

TABLE 4

Stability Results of Succinylcholine Chloride Injection, USP

| | | One Month | | Two Months | | Three Months | | Six Months |
|---|---|---|---|---|---|---|---|---|
| Test | Initial | 2-8° C. | 25° C. | 2-8° C. | 25° C. | 2-8° C. | 25° C. | 2-8° C. |
| Assay (%) | 100.5 | 98.3 | 95.3 | 99.2 | 95.4 | 98.9 | 92.5 | 96.9 |
| Succinic Acid | ND | ND | <LOQ | ND | 0.15 | <LOQ | 0.29 | <LOQ |
| Succinylmonocholine | 0.19 | 0.51 | 1.60 | 0.54 | 2.97 | 0.68 | 4.14 | 1.1 |
| Choline Chloride | 0.09 | 0.14 | 0.71 | 0.14 | 1.53 | NT | NT | 0.44 |
| Total Degradants (%) | 0.42 | 0.71 | 2.37 | 0.87 | 4.84 | N/A | N/A | 1.65 |
| pH | 3.83 | 3.75 | 3.50 | 3.65 | 3.28 | 3.64 | 3.30 | 3.67 |
| Break Force (N) | 4.74 | 5.31 | NT | 5.77 | 7.62 | 4.74 | 4.50 | 6.40 |
| Glide Force (N) | 3.77 | 3.37 | 3.22 | 3.05 | 3.49 | 3.77 | 3.67 | 3.99 |

As can be seen in Table 4, after being stored at 25° C. and 60% relative humidity for two months or at 2° C. to 8° C. for six months, the succinylcholine chloride compositions in the prefilled syringes of Example 4 had a succinylcholine chloride content of greater than 90% of the original concentration, less than 0.2% succinic acid, less than 4.5% succinylmonocholine chloride, less than 2.5% choline chloride, and total impurities less than 8.0%, or less than 6.5%. The syringe physical parameters, such as glide force and days of storage at room temperature preceded by up to fifteen months or up to 18 months of storage at 2° C. to 8° C.

Example 6

In general, analytic protocols for succinylcholine chloride and related chemical impurities are well known in the art, and the following HPLC and IC protocols (which are based on the USP monographs) were used with respect to the Examples and are suitable for use herein.

HPLC for succinylcholine chloride:
Mobile phase: Prepare a 1-liter solution of 100 ml 1 N aqueous tetramethyl ammonium chloride in 900 ml menthol. Adjust to a pH of about 3.0 using HCl.
Standard Solution: Dissolve 88 ml of succinylcholine chloride RS in 4.0 ml of water in a 10 ml volumetric flask and dilute to volume with mobile phase.
Sample preparation: Dissolve 88 ml of sample in 4.0 ml of water in a 10 ml volumetric flask and dilute to volume with mobile phase.
Conventional HPLC system is operated using UV detection at 214 nm and a 4-mm×25-cm, 10 µm column (packing Partisil silica).

IC for choline chloride:
Mobile phase: Generate mobile phase electrolytically using an automatic eluent generator set to 6.45 mM of methanesulfonic acid and IC grade water, where water is contained in plastic bottles, is spurged to degas, and blanketed with nitrogen.
Stock Standard solution: Weigh 20.1 mg of choline chloride RS into a 100 ml flask and dilute to volume with IC grade water to obtain a choline chloride concentration of 201 µg/ml.
Working Standard: Pipet 8.0 ml of standard solution into 50 ml volumetric flask and dilute with IC grade water to obtain a choline chloride concentration of 32.16 µg/ml.
KCl Stock Solution: Dissolve 10 mg KCl in IC grade water to volume in a 100 ml volumetric flask.
Resolution Solution: Mix 7.0 ml of the Stock Standard solution with 5.0 of KCl stock solution and IC grade water to volume in a 100 ml volumetric flask.
Sensitivity Solution: Mix 2.0 ml of the Working Standard with IC grade water in a volumetric flask and dilute to volume.
Drug Product sample preparation: Mix 5.0 ml of drug product (succinylcholine chloride composition) with IC grade water in a 50 ml volumetric flask and dilute to volume.
HPLC column: Dionex Guard Column CG19, 4×50 nm
Analytical column: Dionex CS19, 4×250 nm
Dionex CT-CTC-II cation trap column HPLC for related compounds:
Buffer solution: Mix 3.85 g sodium-1-pentanesulfonate, 2.9 g NaCl, and 10 ml of 1 N sulfuric acid into 990 ml of water, and filter through 0.45 µm filter.
Mobile phase/diluent: Mix 950 ml of Buffer Solution and 50 ml of acetonitrile.
Standard Solution: Mix 25.0 mg of succinylcholine chloride, USP RS with diluent to volume in a 50 ml volumetric flask. Mix 5.0 ml of the resulting solution with diluent and dilute to volume in a 50 ml volumetric flask to obtain a succinylcholine chloride concentration of 50.00 µg/ml.
Suitability Solution: Mix 25 mg citric acid RS and 25 mg succinic acid RS with diluent and dilute to volume in a 50 ml volumetric flask to obtain a citric acid concentration of 500 µg/ml and a succinic acid concentration of 500 µg/ml.
Sensitivity Solution: Mix 2.5 ml of Standard Solution with diluent and dilute to volume in a 25 ml volumetric flask.
Drug Product Sample: Mix 5.0 ml of drug product (succinylcholine chloride composition) with diluent and dilute to volume in a 10 ml volumetric flask.
HPLC column: HPLC system with UV detectors; Waters) (Bridge C18, 4.6×250 nm, 5.0 µm.

We claim:

1. A prefilled syringe containing a premixed succinylcholine chloride composition,
wherein the succinylcholine chloride composition comprises (a) about 10 mg/ml to about 30 mg/ml succinylcholine chloride; (b) a tonicity agent comprising sodium chloride, (c) a pH adjuster comprising hydrochloric acid, sodium hydroxide, or a combination thereof, and (d) water for injection;
wherein the succinylcholine chloride composition has an initial pH of from about 3.0 to about 4.5;
wherein the syringe has a syringe barrel and a syringe tip comprising a cyclic olefin monopolymer (COP) or a cyclic olefin copolymer (COC), a plastic plunger rod, and a plunger rod stopper comprising bromobutyl rubber, chlorobutyl rubber, or an elastomer coated with a poly (ethylene tetrafluoroethylene) (ETFE) film;
wherein the succinylcholine chloride composition in the prefilled syringe contains at least 90% of the initial amount of succinylcholine chloride after storage at 2-8° C. for about 15 months, as determined by High Performance Liquid Chromatography (HPLC); and
wherein the succinylcholine chloride composition in the prefilled syringe does not contain leachables or is substantially free of leachables after storage at 2-8° C. for about 15 months.

2. A prefilled syringe containing a premixed succinylcholine chloride composition,
wherein the succinylcholine chloride composition comprises (a) about 10 mg/ml to about 30 mg/ml succinylcholine chloride; (b) a tonicity agent comprising sodium chloride, (c) a pH adjuster comprising hydrochloric acid, sodium hydroxide, or a combination thereof, and (d) water for injection;
wherein the succinylcholine chloride composition has an initial pH of from about 3.0 to about 4.5;
wherein the syringe has a syringe barrel and a syringe tip comprising a cyclic olefin monopolymer (COP) or a cyclic olefin copolymer (COC), a plastic plunger rod, and a plunger rod stopper comprising bromobutyl rubber, chlorobutyl rubber, or an elastomer coated with a poly (ethylene tetrafluoroethylene) (ETFE) film;
wherein the succinylcholine chloride composition in the prefilled syringe contains at least 90% of the initial amount of succinylcholine chloride after storage at 2-8° C. for about 15 months, as determined by High Performance Liquid Chromatography (HPLC);
wherein the succinylcholine chloride composition in the prefilled syringe contains not more than 6.5% by weight total impurities, not more than 0.2% by weight succinic acid, not more than 2.5% by weight choline chloride, and not more than 4.5% by weight succinylmonocholine chloride after storage at 2-8° C. for about 15 months, as determined by HPLC and/or Ion Chromatography (IC); and
wherein the succinylcholine chloride composition in the prefilled syringe does not contain leachables or is substantially free of leachables after storage at 2-8° C. for about 15 months.

3. The prefilled syringe of claim 1, wherein the succinylcholine chloride composition is present at a concentration of about 20 mg/ml.

4. The prefilled syringe of claim 2, wherein the succinylcholine chloride composition is present in a volume of about 5 ml to about 10 ml.

5. The prefilled syringe of claim 1, wherein the syringe further comprises a luer adapter integral with the syringe tip, and wherein the syringe barrel, syringe tip and luer adapter are a single element comprising COP or COC.

6. The prefilled syringe of claim 1, wherein the succinylcholine chloride composition has an initial osmolality of from about 260 to about 340 mOsm/kg.

7. The prefilled syringe of claim 1, wherein the sodium chloride is present in an amount of from about 4 mg/ml to about 7 mg/ml.

8. The prefilled syringe of claim 7, where the sodium chloride is present in an amount of about 4.5 mg/ml.

9. The prefilled syringe of claim 1, where the syringe has a glide force of less than 7 N and a break force of less than 20 N after storage at 2-8° C. for about 15 months, as determined by mechanical testing.

10. The prefilled syringe of claim 1, where the succinylcholine chloride composition is free of added preservatives.

11. The prefilled syringe of claim 1, wherein the succinylcholine chloride composition has an initial pH of from about 3.3 to about 3.8.

12. A prefilled syringe containing a premixed succinylcholine chloride composition,
wherein the succinylcholine chloride composition comprises (a) about 20 mg/ml succinylcholine chloride; (b) a tonicity agent comprising sodium chloride present in an amount of about 4.5 mg/ml, (c) a pH adjuster comprising hydrochloric acid, sodium hydroxide, or a combination thereof, and (d) water for injection;
wherein the succinylcholine chloride composition has an initial pH of from about 3.0 to about 4.5;
wherein the syringe has a syringe barrel, a syringe tip, and a luer adapter, where the syringe barrel, syringe tip and luer adapter are a single element comprising a cyclic olefin monopolymer (COP) or a cyclic olefin copolymer (COC); a plastic plunger rod; and a plunger rod stopper comprising bromobutyl rubber, chlorobutyl rubber, or an elastomer coated with a poly (ethylene tetrafluoroethylene) (ETFE) film;
wherein the succinylcholine chloride composition in the prefilled syringe contains at least 90% of the initial amount of succinylcholine after storage at 2-8° C. for about 15 months, as determined by High Performance Liquid Chromatography (HPLC); and
wherein the succinylcholine chloride composition in the prefilled syringe does not contain leachables or is substantially free of leachables after storage at 2-8° C. for about 15 months.

13. A prefilled syringe containing a premixed succinylcholine chloride composition,
wherein the succinylcholine chloride composition comprises (a) about 20 mg/ml succinylcholine chloride; (b) a tonicity agent comprising sodium chloride present in an amount of about 4.5 mg/ml, (c) a pH adjuster comprising hydrochloric acid, sodium hydroxide, or a combination thereof, and (d) water for injection;
wherein the succinylcholine chloride composition has an initial pH of from about 3.0 to about 4.5;
wherein the syringe has a syringe barrel, a syringe tip, and a luer adapter, where the syringe barrel, syringe tip and luer adapter are a single element comprising a cyclic olefin monopolymer (COP) or a cyclic olefin copolymer (COC); a plastic plunger rod; and a plunger rod stopper comprising bromobutyl rubber, chlorobutyl rubber, or an elastomer coated with a poly (ethylene tetrafluoroethylene) (ETFE) film;
wherein the succinylcholine chloride composition in the prefilled syringe contains at least 90% of the initial amount of succinylcholine after storage at 2-8° C. for about 15 months, as determined by High Performance Liquid Chromatography (HPLC);
wherein the succinylcholine chloride composition in the prefilled syringe contains not more than about 6.5% by weight total impurities, not more than 0.2% by weight succinic acid, not more than 2.5% by weight choline chloride, and not more than 4.5% by weight succinylmonocholine chloride after storage at 2-8° C. for about 15 months, as determined by HPLC and/or Ion Chromatography (IC); and
wherein the succinylcholine chloride composition in the prefilled syringe does not contain leachables or is substantially free of leachables after storage at 2-8° C. for about 15 months.

14. A kit comprising:
(a) the prefilled syringe of claim 12; and
(b) tamper-evident flexible plastic packaging enveloping the prefilled syringe, wherein the packaging comprises polyester film.

15. The prefilled syringe of claim 1, wherein the succinylcholine chloride composition in the prefilled syringe contains at least 90% of the initial amount of succinylcholine chloride after storage at 2-8° C. for about 18 months, as determined by HPLC.

16. The prefilled syringe of claim 2, wherein the succinylcholine chloride composition in the prefilled syringe contains at least 90% of the initial amount of succinylcholine chloride after storage at 2-8° C. for about 18 months, as determined by HPLC and wherein the succinylcholine chloride composition contains not more than 6.5% by weight total impurities, not more than 0.2% by weight succinic acid, not more than 2.5% by weight choline chloride, and not more than 4.5% by weight succinylmonocholine chloride after storage at 2-8° C. for about 18 months, as determined by HPLC and/or IC.

17. The prefilled syringe of claim 2, wherein the succinylcholine chloride composition is present at a concentration of about 20 mg/ml.

18. The prefilled syringe of claim 2, wherein the syringe further comprises a luer adapter integral with the syringe tip, and wherein the syringe barrel, syringe tip and luer adapter are a single element comprising COP or COC.

19. The prefilled syringe of claim 2, wherein the succinylcholine chloride composition has an initial osmolality of from about 260 to about 340 mOsm/kg.

20. The prefilled syringe of claim 2, wherein the sodium chloride is present in an amount of from about 4 mg/ml to about 7 mg/ml.

21. The prefilled syringe of claim 2, where the succinylcholine chloride composition is free of added preservatives.

22. The prefilled syringe of claim 2, wherein the succinylcholine chloride composition has an initial pH of from about 3.3 to about 3.8.

23. The prefilled syringe of claim 12, wherein the succinylcholine chloride composition in the prefilled syringe contains at least 90% of the initial amount of succinylcholine chloride after storage at 2-8° C. for about 18 months, as determined by HPLC.

24. The prefilled syringe of claim 13, wherein the succinylcholine chloride composition in the prefilled syringe contains at least 90% of the initial amount of succinylcholine chloride after storage at 2-8° C. for about 18 months, as determined by HPLC and wherein the succinylcholine chloride composition contains not more than 6.5% by weight total impurities, not more than 0.2% by weight succinic acid, not more than 2.5% by weight choline chloride, and not more than 4.5% by weight succinylmonocholine chloride after storage at 2-8° C. for about 18 months, as determined by HPLC and/or IC.

25. The prefilled syringe of claim 12, wherein the succinylcholine chloride composition has an initial pH of from about 3.3 to about 3.8.

26. The prefilled syringe of claim 25, wherein the succinylcholine chloride composition has a pH of from about 3.3 to about 3.8 after storage at 2-8° C. for about 15 months.

27. The prefilled syringe of claim 13, wherein the succinylcholine chloride composition has an initial pH of from about 3.3 to about 3.8.

28. The prefilled syringe of claim 27, wherein the succinylcholine chloride composition has a pH of from about 3.3 to about 3.8 after storage at 2-8° C. for about 15 months.

29. The prefilled syringe of claim 11, wherein the succinylcholine chloride composition has a pH of from about 3.3 to about 3.8 after storage at 2-8° C. for about 15 months.

30. The prefilled syringe of claim 22, wherein the succinylcholine chloride composition has a pH of from about 3.3 to about 3.8 after storage at 2-8° C. for about 15 months.

31. The prefilled syringe of claim 2, wherein the succinylcholine chloride composition in the prefilled syringe does not contain leachables after storage at 2-8° C. for about 15 months.

32. The prefilled syringe of claim 2, wherein the succinylcholine chloride composition in the prefilled syringe is substantially free of leachables after storage at 2-8° C. for about 15 months.

\* \* \* \* \*